United States Patent
Ferko et al.

(10) Patent No.: US 9,522,008 B2
(45) Date of Patent: Dec. 20, 2016

(54) SYSTEM AND METHOD OF BONE PREPARATION

(71) Applicant: Howmedica Osteonics Corp., Mahwah, NJ (US)

(72) Inventors: Michael C. Ferko, Warwick, NY (US); Vincent Alipit, Nanuet, NY (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 14/640,477

(22) Filed: Mar. 6, 2015

(65) Prior Publication Data

US 2015/0173777 A1 Jun. 25, 2015

Related U.S. Application Data

(62) Division of application No. 12/898,937, filed on Oct. 6, 2010, now abandoned.

(51) Int. Cl.
*A61B 17/16* (2006.01)
*A61B 17/17* (2006.01)

(52) U.S. Cl.
CPC ......... *A61B 17/1617* (2013.01); *A61B 17/164* (2013.01); *A61B 17/1659* (2013.01); *A61B 17/17* (2013.01)

(58) Field of Classification Search
CPC ................ A61B 17/17; A61B 17/1703; A61B 2019/508
USPC ........................................ 606/79, 80, 87, 89
See application file for complete search history.

(56) References Cited

U.S. PATENT DOCUMENTS

| | | | |
|---|---|---|---|
| 5,496,324 A | 3/1996 | Barnes | |
| 5,908,423 A | 6/1999 | Kashuba et al. | |
| 5,957,925 A | 9/1999 | Cook et al. | |
| 5,976,147 A | 11/1999 | LaSalle et al. | |
| 6,342,056 B1 | 1/2002 | Mac-Thiong et al. | |
| RE38,058 E | 4/2003 | Fallin | |
| 6,554,838 B2 | 4/2003 | McGovern et al. | |
| 6,702,822 B1 | 3/2004 | Noiles et al. | |
| 6,949,101 B2 | 9/2005 | McCleary et al. | |
| 7,008,430 B2 | 3/2006 | Dong et al. | |
| 7,090,677 B2 | 8/2006 | Fallin et al. | |
| 7,141,053 B2 | 11/2006 | Rosa et al. | |
| 7,255,702 B2 | 8/2007 | Serra et al. | |
| 7,393,355 B2 | 7/2008 | Tulkis et al. | |
| 7,485,119 B2 | 2/2009 | Thelen et al. | |
| 7,615,054 B1 * | 11/2009 | Bonutti ............... | A61B 17/025 606/87 |
| 7,632,273 B2 | 12/2009 | Schnieders et al. | |
| 7,695,477 B2 | 4/2010 | Creger et al. | |
| 7,785,328 B2 | 8/2010 | Christie et al. | |

(Continued)

*Primary Examiner* — Anu Ramana
(74) *Attorney, Agent, or Firm* — Lerner, David, Littenberg, Krumholz & Mentlik, LLP (57) ABSTRACT

The invention includes a system, method and kit for preparation of a bone. One aspect of the present invention is a bone preparation system comprising a cutting instrument and a guiding element. The cutting instrument includes a distal attachment feature and a distal region. The guiding element includes a proximal attachment feature and a guiding surface. When the proximal attachment feature of the guiding element is engaged with the distal attachment feature of the cutting instrument, the cutting instrument can pivot about the proximal attachment feature until the distal region contacts the guiding surface.

11 Claims, 11 Drawing Sheets

(56) References Cited

U.S. PATENT DOCUMENTS

| | | |
|---|---|---|
| 8,167,882 B2 | 5/2012 | Sackett et al. |
| 2003/0171756 A1 | 9/2003 | Fallin et al. |
| 2003/0187449 A1 | 10/2003 | McCleary et al. |
| 2004/0153081 A1 | 8/2004 | Tulkis et al. |
| 2007/0226986 A1* | 10/2007 | Park ............... A61B 17/155 29/592 |
| 2008/0147071 A1 | 6/2008 | Serra et al. |
| 2008/0294169 A1 | 11/2008 | Scott et al. |
| 2009/0222008 A1 | 9/2009 | Hogg et al. |
| 2009/0222015 A1* | 9/2009 | Park ............... A61B 17/175 606/89 |
| 2010/0023066 A1 | 1/2010 | Long et al. |
| 2010/0042103 A1 | 2/2010 | Rasmussen |
| 2010/0063592 A1 | 3/2010 | Dwyer et al. |
| 2010/0069908 A1 | 3/2010 | Sidebotham et al. |
| 2010/0114323 A1 | 5/2010 | Deruntz et al. |

\* cited by examiner

SYSTEM AND METHOD OF BONE PREPARATION

CROSS-REFERENCE TO RELATED APPLICATIONS

This application is a divisional of U.S. application Ser. No. 12/898,937 filed Oct. 6, 2010 the disclosure of which is incorporated herein by reference.

BACKGROUND OF THE INVENTION

The present invention relates to a bone reaming system, and more particularly, to an apparatus and method for preparing specific geometries in the metaphyseal region of long bones.

Orthopedic surgery has been prevalent in recent years and the number of joint arthroplasty procedures is projected to grow exponentially in the future. Total knee replacement (TKR) is an example of joint arthroplasty. In TKR, the end surfaces of the femoral and tibial bones are resected and replaced with implants that may be made from metal, ceramic, polyethylene, or some combination thereof. In this procedure, the femoral and tibial implants may be fixed to the bone using cement, cementless biologic fixation or other known fixation means. While good TKR survivorship has been reported, it is known that these procedures may fail for reasons including incorrect alignment, loosening, osteolysis, infection, and the like. If a TKR procedure fails, a revision TKR procedure may be required.

In revision TKR, the primary implant components typically need to be removed, leaving defects or voids in the metaphyseal regions of the long bones on which they were implanted. Defects may be the result of removing the implants, the cement, other fixation means such as screws, or bone regions compromised by infection. The void size and geometry are unique for each patient and it is critical to augment these defect regions to ensure proper structural support for revision TKR implants.

In these revision TKR procedures, the augments available to address these bone defects are generally offered in limited sizes and shapes which do not consider the unique defect geometries of a particular patient. At least in part, the limitation of augment offerings is due to inability of current preparation instrument systems to prepare complex and non-uniform geometries. Thus, it is common place for patients to have excessive bone removed from their specific defect region in order to receive standard augment prostheses. Moreover, in some cases, an impaction based preparation technique such as broaching is used to prepare a bone defect region during revision surgery. Given that the bone in the defect region is already compromised, this impaction technique may lead to bone fractures which further worsen the patient condition and require addition intervention.

Therefore there exists a need for bone preparation system that will allow for complex and non-uniform geometries to be created during a preparation of the bone using non-impaction means.

BRIEF SUMMARY OF THE INVENTION

One aspect of the present invention is a bone preparation system comprising a cutting instrument and a guiding element. The cutting instrument includes an attachment feature and a first region. The guiding element includes an attachment feature and a guiding surface. When the attachment feature of the guiding element is engaged with the distal attachment feature of the cutting instrument, the cutting instrument can rotate and pivot about the guiding element. Contact between the first region and the guiding surface determines the amount of pivot of the cutting instrument about the guiding element.

Alternate embodiments of the bone preparation system may include any of, or any combination of the following: the cutting instrument attachment feature is a distal attachment feature and the first region is a distal region, the guiding surface attachment feature is a proximal attachment feature; the distal region of the cutting instrument may be comprised of a distal end and a distal surface; the guiding surface of the guiding element may extend 360 degrees around or around a portion of the attachment feature of the guiding element; the guiding surface may be derived from an outer profile of an augment implant which may be derived from a pre-operative patient specific imaging process; the guiding element may further include an aperture designed to engage a stem wherein the stem may include a cutting feature; the central axis of the guiding element, aperture and stem have various alignments; or the attachment feature of the guiding element may be a sphere and the distal attachment feature is a spherical female indentation.

Another aspect of the present invention is a method of bone preparation. Here, a guiding element is inserted into the canal of a bone and a cutting instrument is attached to the guiding element. The bone is prepared by pivoting the cutting instrument about the guiding element. The cutting instrument and guiding element are removed from the prepared bone.

Alternate embodiments of the method bone preparation system may include any of, or any combination of the following methods: preparing the canal of the bone using a reamer, engaging the guiding element with the reamer, inserting a prosthetic implant into the prepared bone, rotating the cutting instrument about the central axis, pivoting the cutting instrument about the guiding element, imaging of the patient, or developing a pre-operative patient specific implant based on the imaging of the bone of a patient.

A further aspect of the present invention is a bone preparation kit comprising an augment implant and a guiding element. The augment implant is for the metaphyseal region of a long bone. The guiding element includes a guiding surface where the guiding surface is derived from an outer profile of the augment implant.

Alternate embodiments of the bone preparation kit may further comprise any of the following: the augment implant includes a geometry based on patient imaging, the guiding surface includes a distal having at least one fixation feature, the guiding element further includes an aperture designed to engage a stem.

BRIEF DESCRIPTION OF THE DRAWINGS

The present invention will be better understood on reading the following detailed description of non-limiting embodiments thereof, and on examining the accompanying drawings, in which.

DETAILED DESCRIPTION

As used herein, the term "distal" means more distant from the heart and the term "proximal" means closest to the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body.

Figure 1:
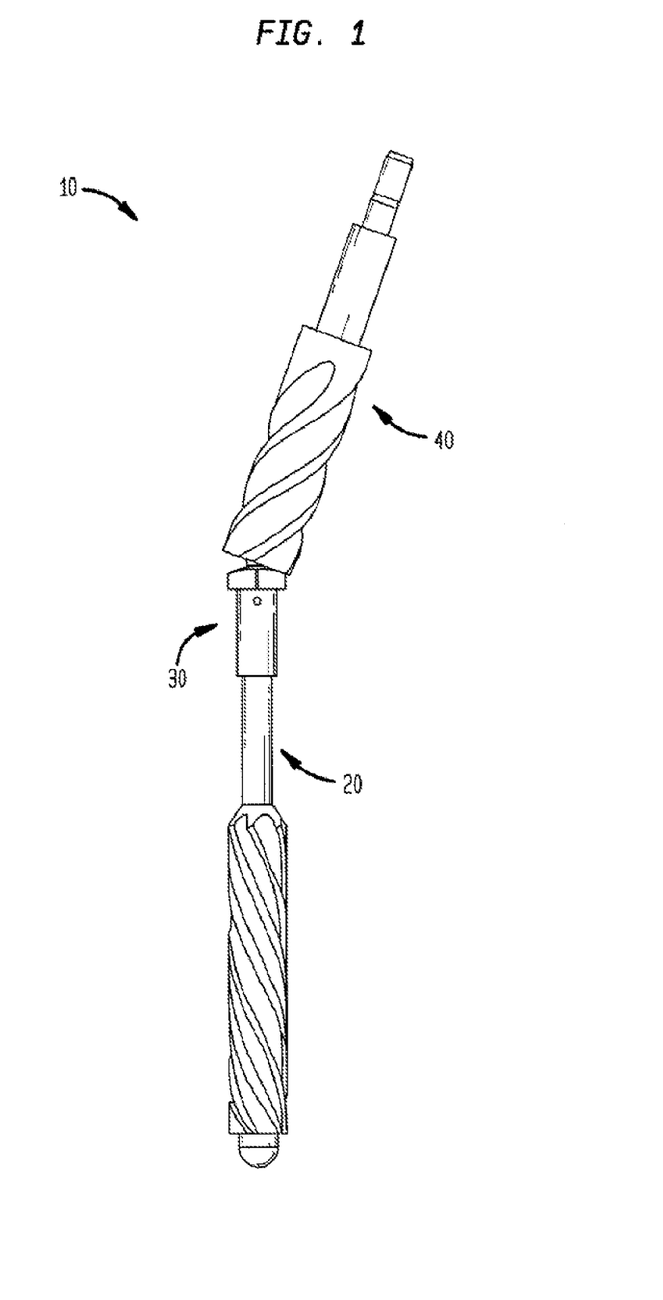
FIG. 1 is a perspective view of a bone preparation system in accordance with one embodiment of the present invention.
Figure 2:
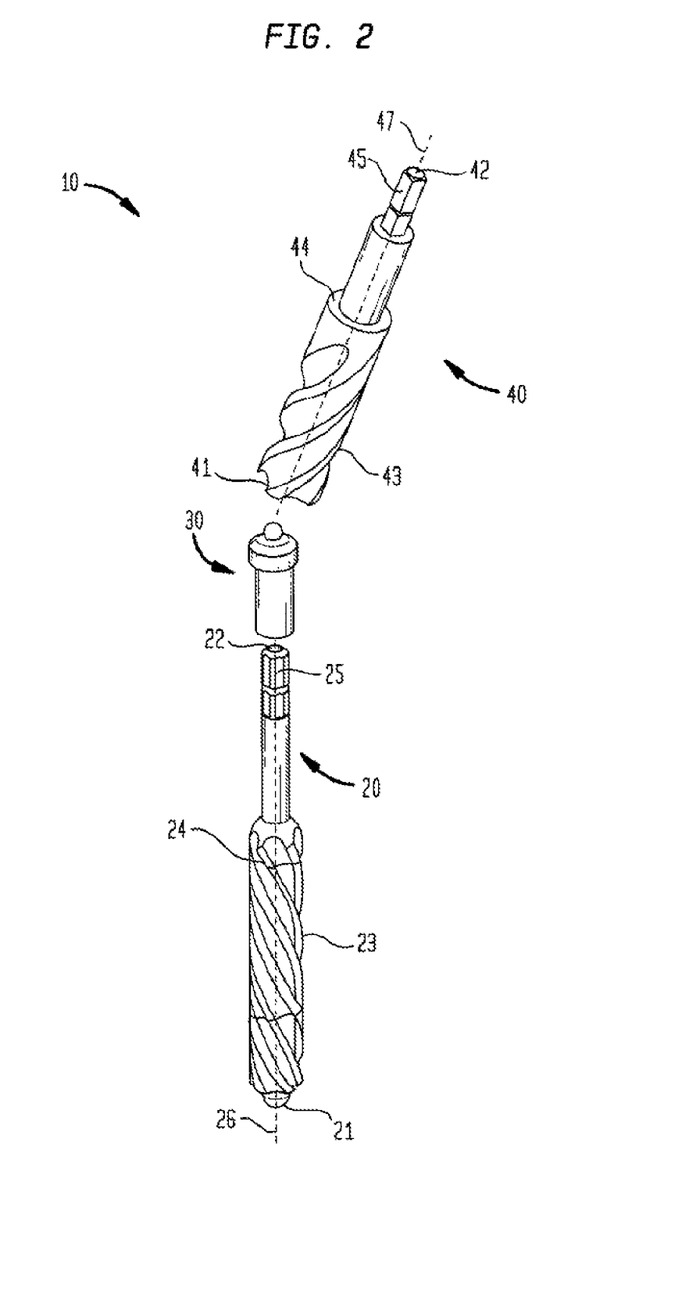
FIG. 2 is an exploded view of the bone preparation system shown in FIG. 1.

Referring to the drawings, FIGS. 1-2 illustrate one embodiment bone preparation system 10 including a stem 20, guiding element 30 and a cutting instrument 40. The stem 20 has a distal end 21, proximal end 22 and a central axis 26. The stem 20 is designed to fit within the intramedullary canal of a long bone, for example, the tibia (shown in FIGS. 12 and 13). The stem 20 may include features such as an outer profile 23, depth references 24 and attachment geometries 25 for interfacing with other instruments. The attachment geometries 25 are designed to allow for assembly with other instruments as well as to provide rotational constraint during subsequent bone preparation, which will be further described. In the embodiment shown, a powered reaming instrument, which is not shown but is known in the art, would interface with the attachment geometries 25 and rotate the stem 20 about its central axis 26 within the intramedullary canal. Further, in this embodiment, outer profile 23 is a cutting surface that prepares the intramedullary canal as the stem 20 rotates. In an alternate embodiment, the stem 20 may have a smooth outer profile 23 dimensioned to reference a previously prepared intramedullary canal. Further in this alternate embodiment, the attachment geometries 25 may allow interface with an insertion-extraction instrument. In one or more embodiments, depth references 24 may be located anywhere on stem 20 and serve as an indicator of location to the user.

The cutting instrument 40 has a distal end 41, a proximal end 42 and a central axis 47. Cutting instrument 40 may include features such as an outer profile 43, a depth reference 44 and proximal attachment geometries 45 for interfacing with other instruments. Outer profile 43 preferably contains a cutting geometry and may have a single diameter throughout the cutting region. In alternate embodiments, outer profile 43 may have a non-constant diameter, stepped diameter or other geometric configuration to allow variable bone preparation. In the embodiment shown, cutting instrument 40 is a reamer and a powered reaming instrument would interface with the proximal attachment geometries 45 to rotate the reamer about central axis 47 to prepare the bone. In other embodiments, other instruments may interface with attachment geometries 45 to allow for rotational bone preparation, such as devices facilitating manual rotation. Further, in alternate embodiments, cutting instrument 40 may be a burr or other cutting geometry that rotates in order to prepare bone.

Figure 3:
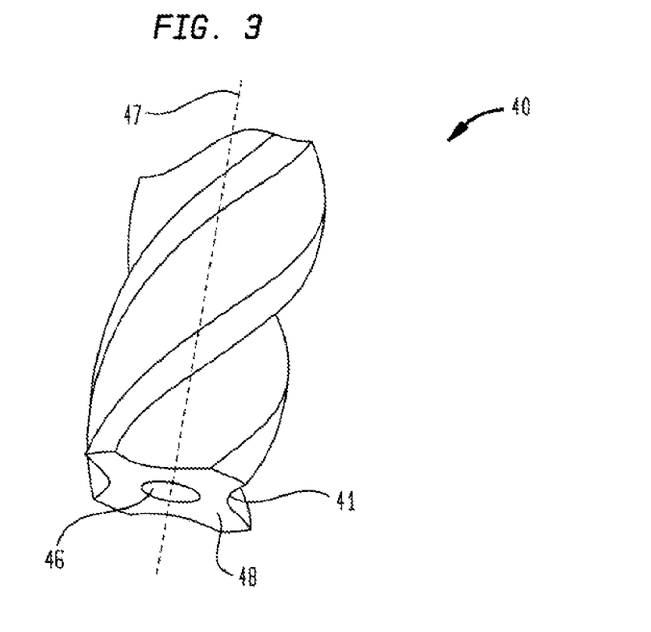
FIG. 3 is an enlarged perspective view of a portion of a cutting instrument included in the bone preparation system shown in FIG. 1.

Depth reference 44 serves as a location indicator to the user and can take the form or engraved marks, steps, or the like. In the particular embodiment shown in FIGS. 1 and 2, depth reference is a step. Further, there may be multiple depth references 44 on the cutting instrument 40. FIG. 3 further illustrates the distal region of cutting instrument 40, which includes a distal surface 48 and a distal end 41. In the embodiment shown the attachment feature 46 is a spherical female indentation designed to engage with a male feature of guiding element 30 (described below). The stem 20, guiding element 30 and cutting instrument 40 are constructed of known instrument or implant material, such as stainless steel or titanium.

Figure 4:
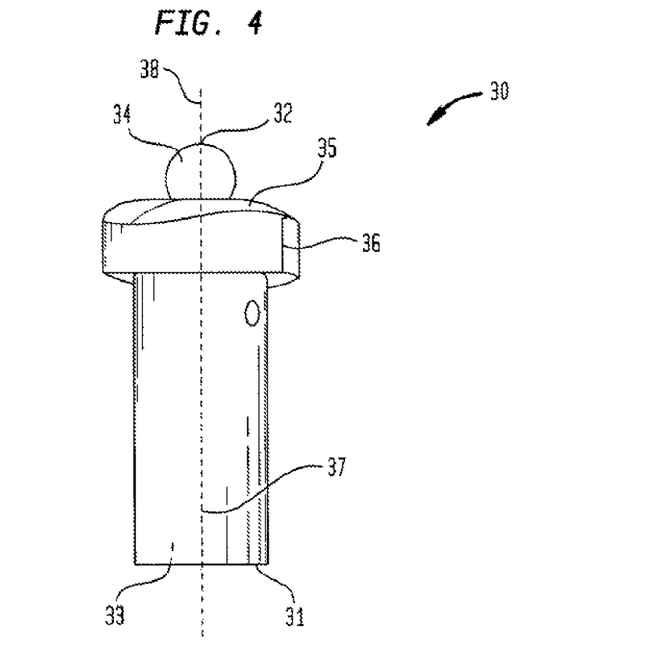
FIG. 4 is a perspective view of a guiding element included in the bone preparation system shown in FIG. 1.

FIG. 4 illustrates, in more detail, guiding element 30, which includes a distal end 31 and proximal end 32. Distal end 31 may have an aperture 33 including an aperture central axis 37. Preferably, aperture 33 is designed to interface over proximal end 22 of stem 20, thereby engaging attachment geometries 25. When engaged, central axis 26 of stem 20 is aligned with the aperture central axis 37. In the depicted embodiment, guiding element 30 also preferably includes an alignment feature 36 taking the form of an engraved line which allows for orientation reference of the guiding element 30 as it is assembled with stem 20. Of course, in other embodiments, alignment feature 36 may be different elements, including, a notch, protrusion, or the like. Also in other embodiments, guiding element 30 may include a structure designed to affix it with stem 20. For example, a ball/detent or male/female connection may be employed.

Figure 5:
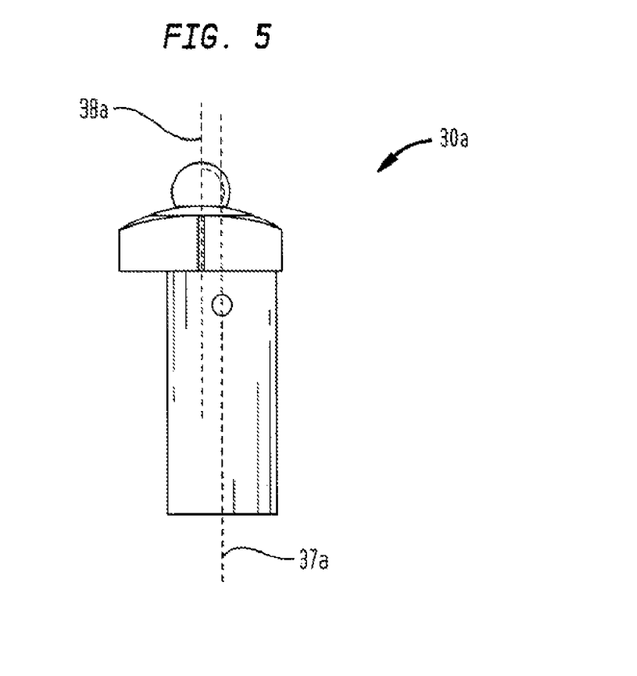
FIG. 5 is a perspective view of an alternate embodiment of a guiding element.

Guiding element 30 in FIG. 4 also includes a proximal attachment feature 34 designed to interface with attachment feature 46 of a cutting instrument 40. In the embodiment shown, the proximal attachment feature 34 is a protrusion having a spherical geometry and includes an attachment feature central axis 38 that is aligned with aperture central axis 37. In an alternate embodiment shown in FIG. 5, attachment feature central axis 38a may be offset and therefore not aligned with the aperture central axis 37a. Further regarding guiding element 30, proximal attachment feature 34 and attachment feature 46 may be other known mechanisms used for removable attachment. In addition, while attachment features 34 and 46 are shown as male and female elements, respectively, this may be the opposite in other embodiments. In other words, cutting instrument 40 could include a male attachment feature, while guiding element 30 includes a female attachment feature.

The guiding element 30 may further include a guiding surface 35 designed to allow for a specified bone preparation. The geometry of guiding surface 35 may be derived from a pre-operative scan, such as Magnetic Resonance Imaging (MRI), Computed Tomography (CT), X-ray or similar know technology. Here, a bone model is generated from the pre-operative scan. The guiding surface 35 is preferably derived from the bone model as a mathematically sweeping geometry between multiple cross sections of a patient specific defect and can range from zero to 360 degrees around the attachment feature central axis 38. In an alternate embodiment, guiding surface 35 may be derived from a standard augment implant design.

As noted above, proximal attachment feature 34 of the guiding element 30 is preferably engaged with the attachment feature 46 of the cutting element 40. When engaged, the attachment feature central axis 38 intersects with the central axis 47 of the cutting instrument 40. During bone preparation, the cutting instrument 40 is angled until the distal end 41 or distal surface 48 of the distal region engages with the guiding surface 35, thus establishing an outer bound for the bone preparation.

Further on the bone preparation, cutting instrument 40 rotates its central axis 47, and also pivots about proximal attachment feature 34. Then, as either, or both the distal end 41 or distal surface 48 references the path of guiding surface 35, thus establishing an outer bounds for the bone preparation. The prepared bone geometry governed by guiding surface 35 is based on an augment implant designed to fill a patient specific defect and may be any unique geometry, including symmetric, asymmetric or offset.

In this bone preparation system, the geometry of the bone preparation is thusly governed by the geometry of the guiding surface 35, which is located distal to the cutting instrument 40. Further, the guiding surface 35 is located within the cortical perimeters of a long bone. Also of note, the attachment feature central axis 38 of guiding surface 35 may or may not be aligned with the central axis 26 of stem 20 which allows for asymmetric, offset and non-uniform preparation of the metaphyseal region of the long bone.

The stem 20, guiding element 30 and cutting instrument 40 are illustrated in FIGS. 1-4 as independent structures. Other embodiments of this invention may include: the stem 20 and guiding element 30 being a single structure, the guiding element 30 and the cutting instrument 40 being a single structure, or the stem 20, guiding element 30 and cutting instrument 40 being a single instrument structure.

Figure 6:
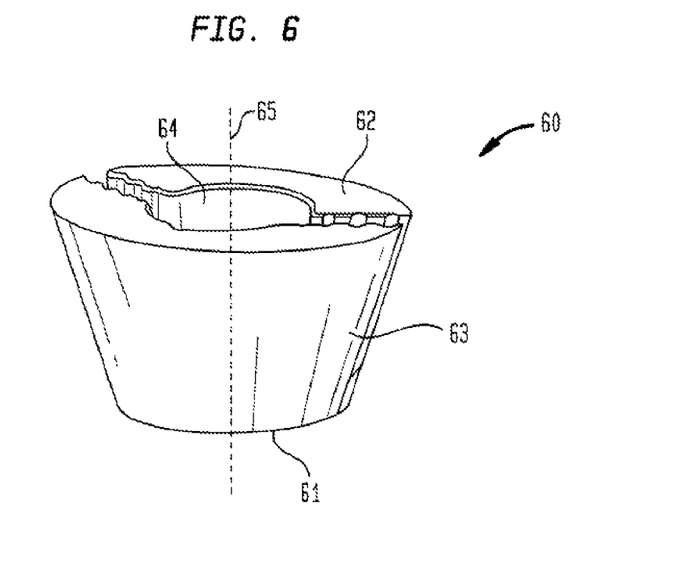
FIG. 6 is a perspective view of a tibial augment in accordance with one embodiment of the present invention.

FIG. 6 illustrates a tibial augment 60 having a distal end 61 and a proximal end 62. Tibial augment 60 is preferably utilized to replace cancellous bone that was removed as the result of primary TKR implant removal, infection or the like. The tibial augment 60 is designed to provide the structural support for the revision TKR baseplate components. It has an outer profile 63, a central aperture 64 and a central axis 65. Central aperture 64 is designed to interface with prosthesis such as revision TKR baseplate component 70, as shown in FIG. 6.

Figure 7:
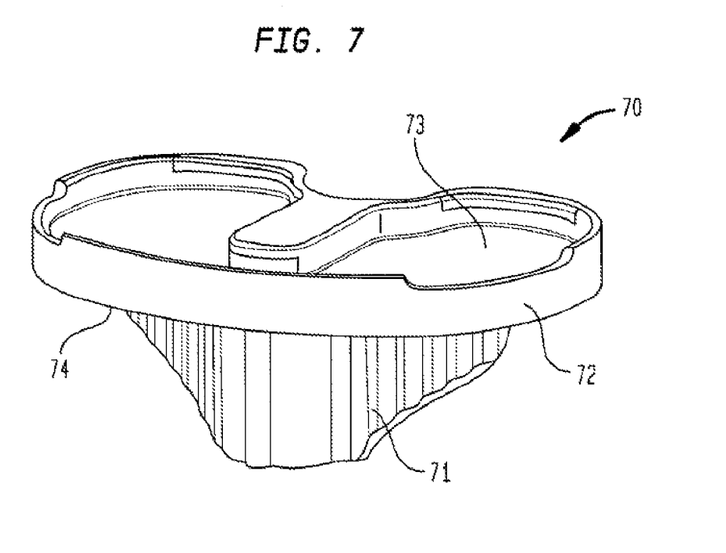
FIG. 7 is a perspective view of tibial baseplate implant in accordance with one embodiment of the present invention.
Figure 8:
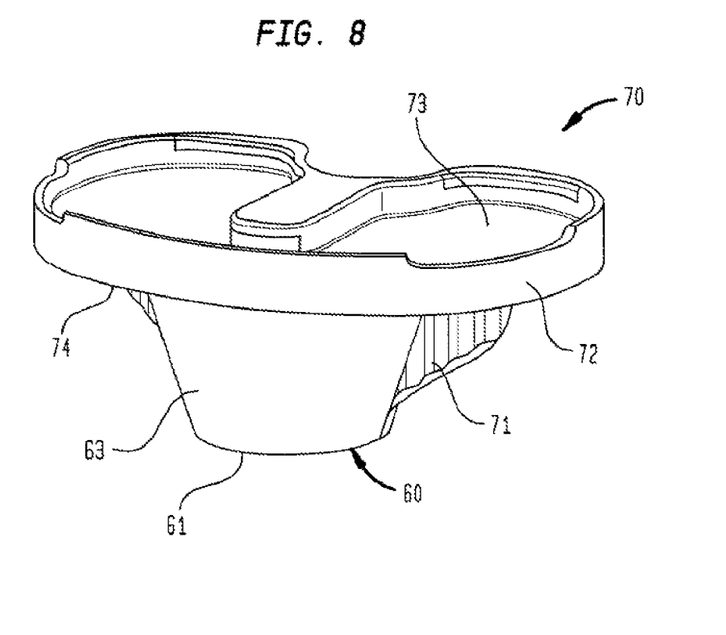
FIG. 8 is a perspective view of the tibial augment shown in FIG. 6 assembled with the tibial baseplate implant shown in FIG. 7.

As shown in FIG. 7, the tibial baseplate component 70 may include a distal feature 71, such as a keel, and a tray component 72 that has a proximal surface 73 and a distal surface 74. FIG. 8 illustrates an example of a tibial augment 60 assembled with a tibial baseplate component 70. A tibial augment may be assembled with tibial baseplate component 70 using cement, mechanical attachment or other known means.

Figure 9:
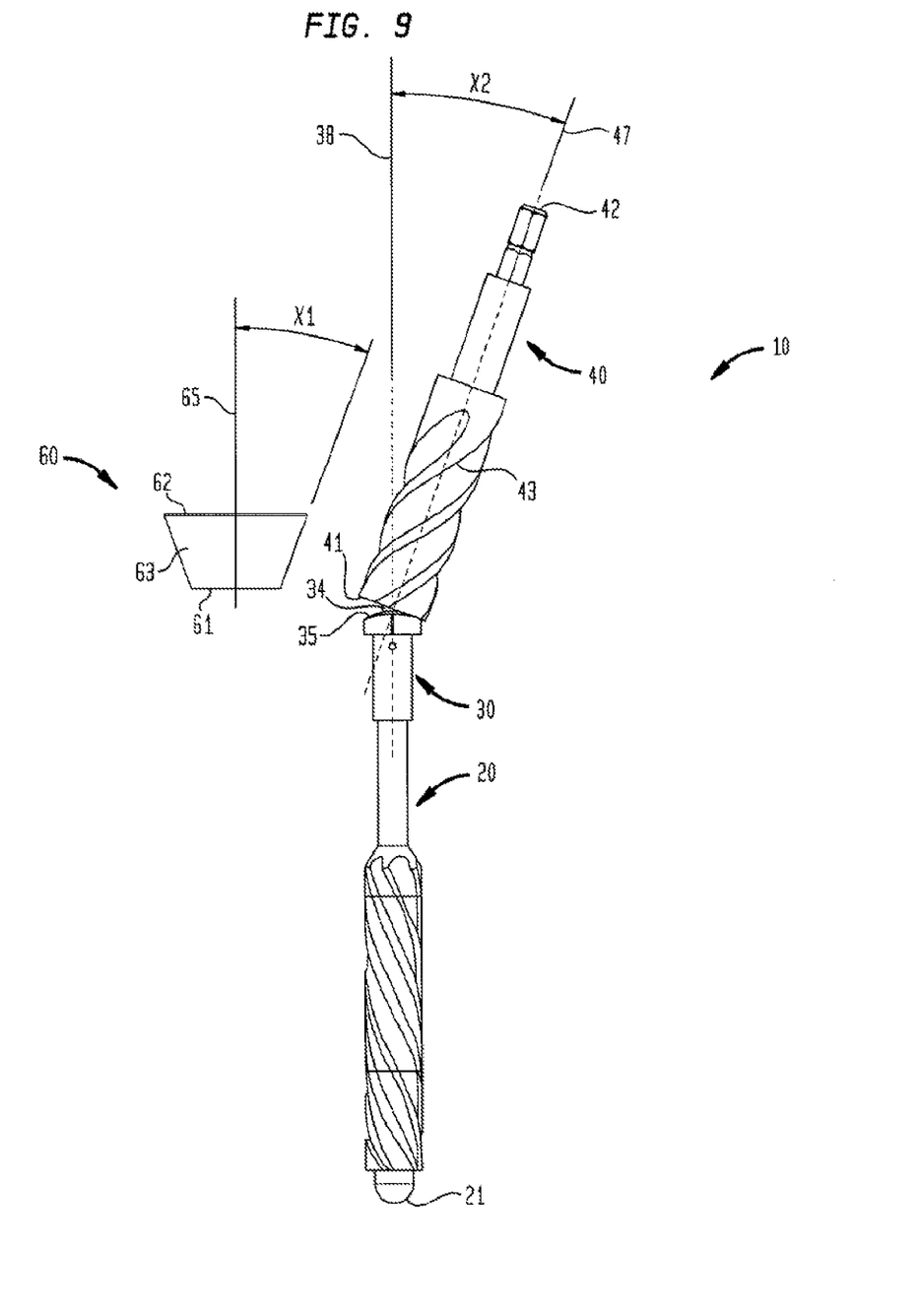
FIG. 9 is a view illustrating the relationship of the geometry of the tibial augment shown in FIG. 6 to the bone preparation system shown in FIG. 1.

FIG. 9 shows the relationship between the geometry of tibial augment 60 and bone preparation system 10, in particular, the geometrical relationship between outer profile 63 of tibial augment 60 and the guiding surface 35 of guiding element 30. Here, tibial augment 60 has an outer profile 63 defined by an angle X1 measured from a central axis 65. Guiding surface 35 has a geometry that allows for a defect specific path for the cutting instrument 40. Attachment feature 46 of cutting instrument 40 is engaged to proximal attachment feature 34 and distal end 41 references guiding surface 35. X2 represents an angular relationship between the attachment feature central axis 38 and cutting instrument 40 central axis 47. Angles X1 and X2 have a mathematical relation with respect to central axes 65 and 38.

Figure 10:
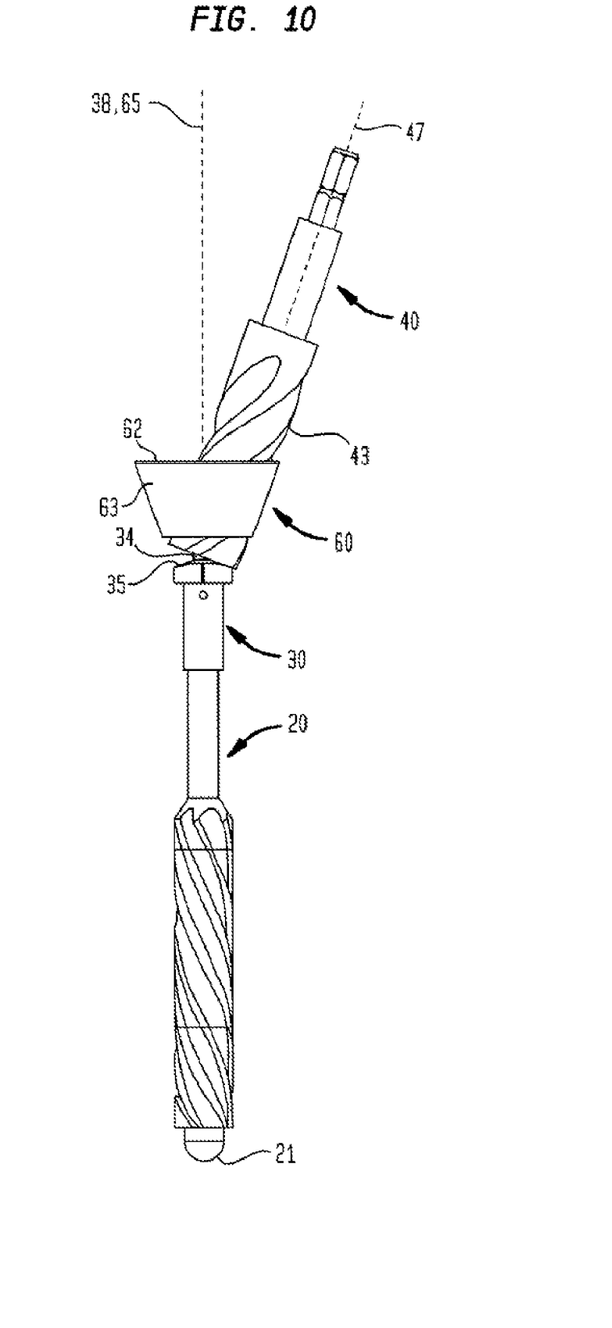
FIG. 10 is another view illustrating the relationship of the geometry of the tibial augment shown in FIG. 6 to the bone preparation system shown in FIG. 1.

FIG. 10 provides an overlayed perspective of the relationship between the specific outer profile 63 of tibial augment 60 and the outer bounds of the bone preparation governed by the guiding surface 35. This relationship is demonstrated by aligning the attachment feature central axis 38 and the central axis 65 of the tibial augment 60. It is understood the mathematical relationship relates to multi-dimensional implant structures and may involve any unique geometry that would be different from patient to patient.

Guiding element 30 may be distributed as a standard instrument, a disposable instrument or a custom single use instrument. With a standard augment product offering, such as a tibial augment 60, the guiding element 30 may be included as a standard instrument in an instrument kit. Also with a standard tibial augment 60, the guiding element 30 may be disposable instrument, designed for a single use, and to be used with standard stem 20 and cutting instrument 40. In an alternate scenario, patient specific augments and may be created using scans, such as a pre-operative MRI, CT, X-ray or any combination thereof. Then a patient specific kit would be provided which includes, for example, a patient specific tibial augment 60, and a guiding element 30. The patient specific preparation would be guided thru the unique guiding surface 35 geometry that is designed to match patient specific augment geometry. Here, the patient specific tibial augment and augment specific guiding element 30 may be packaged together for a specific surgery.

Figure 11:
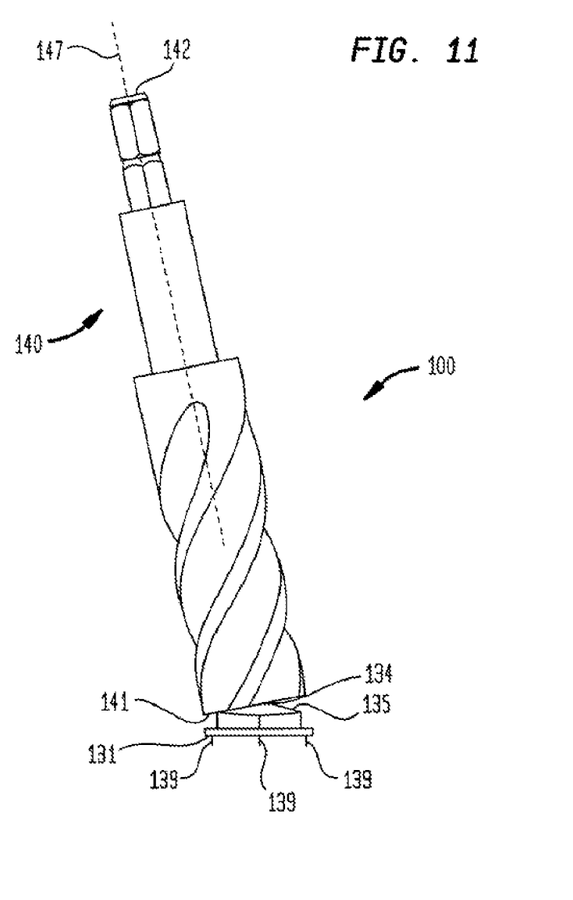
FIG. 11 is a perspective view of an alternate embodiment bone preparation system in accordance with the present invention.
Figure 12:
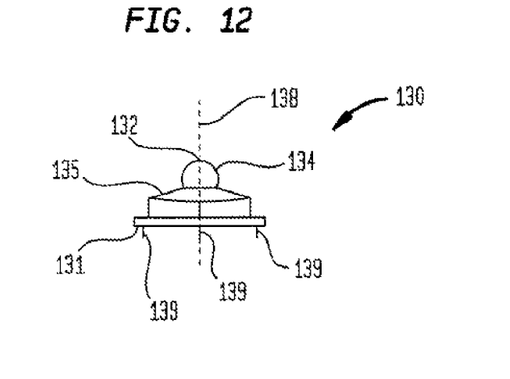
FIG. 12 is a perspective view of a guiding element included in the bone preparation system shown in FIG. 11.

FIGS. 11-12 illustrate an alternate embodiment of a bone preparation system 100 consisting of a cutting instrument 140 and a guiding element 130. While each are not discussed, like elements to that of system 10 are labeled in FIGS. 11 and with like reference numerals within the 100-series of numbers. For instance, similar to the embodiment previously described, cutting instrument 140 engages with an proximal attachment feature 134 on the guiding element 130. The cutting instrument 140 rotates about its central axis 147, and then pivots about attachment element 134 until either the distal end 141 or distal surface 148 contacts guiding surface 135, thus establishing the outer bounds for the bone preparation. The significant difference with this alternate embodiment is that the guiding element 130 does not get assembled with a stem component 20, but rather attaches directly to bone within the intermedullary canal. For example if the intermedullary canal is prepared to a certain depth using a reamer instrument or the like, the guiding element 130 would be placed at the interface between the prepared intermedullary bone and the unprepared intermedullary bone where there is a natural cortical bone "shelf". Fixation features 139 affix guiding element 130 to the bone and provides rotational constraint during bone preparation. These fixation features are shown as teeth, but may be other known fixation features, such as screws, pins or the like.

Figure 13:
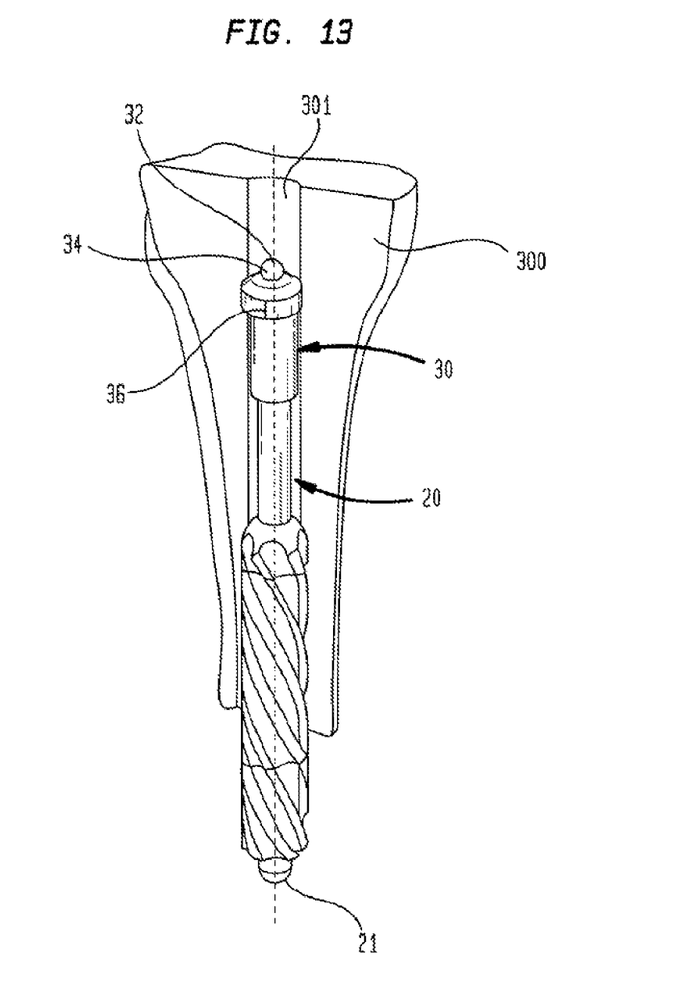
FIG. 13 is a cross-sectional view of a tibial bone with a portion of the bone preparation system shown in FIG. 1 included therein.
Figure 14:
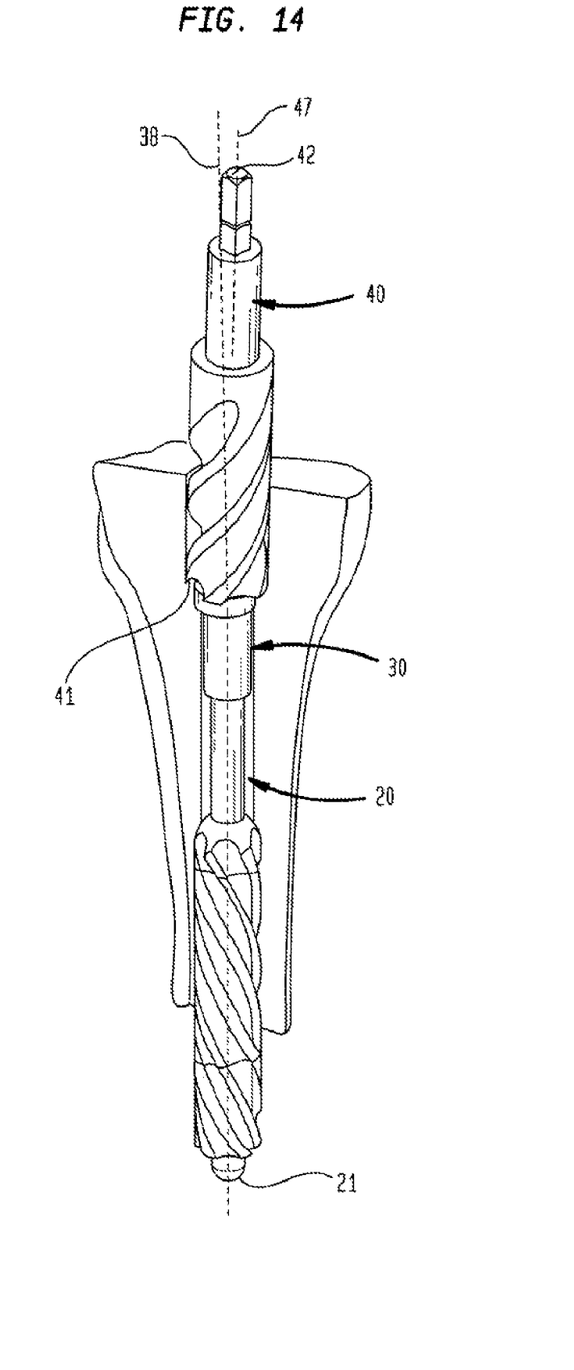
FIG. 14 is a cross-sectional view of a tibial bone with the bone preparation system shown in FIG. 1 included therein.
Figure 15:
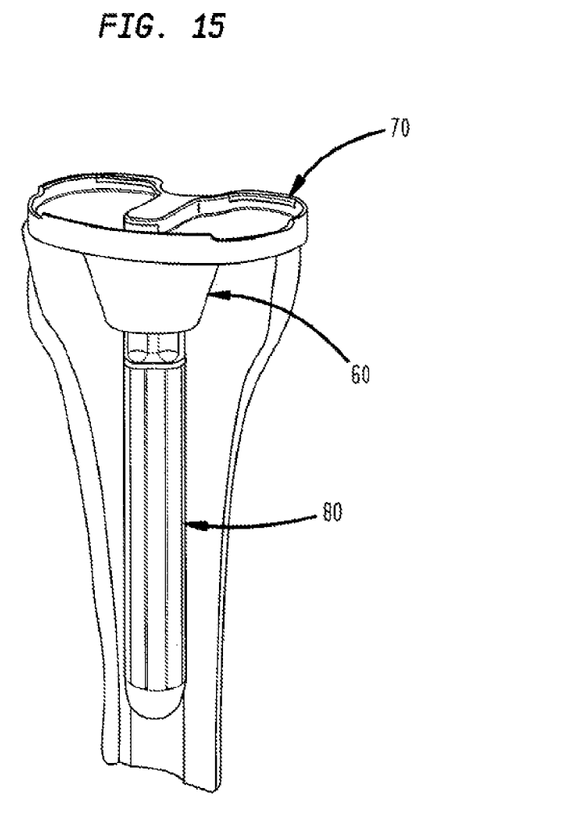
FIG. 15 is a cross-sectional view of a tibial bone with the construct shown in FIG. 8 implanted thereon.

A method of preparing a bone utilizing system 10 is illustrated in FIGS. 13-15. In this method, the intermedullary canal of tibial long bone 300 has been prepared using stem 20, resulting in a prepared intramedullary canal region 301. This is best shown in FIG. 13, where stem 20 remains in the prepared central region 301. Aperture 33 and alignment feature 36 of guiding element 30 are then removably attached with the attachment geometry 25 of stem 20, as shown in FIG. 14. Also shown in that figure, the attachment feature of cutting instrument 40 is then assembled to proximal attachment feature 34 of guiding element 30. Cutting instrument 40 is then rotated about its central axis 47, thus establishing a rotational cutting motion. The cutting instrument is then angled, by pivoting about attachment feature central axis 38, until distal end 41 contacts guiding surface 35. The rotating and pivoting of cutting instrument 40 is continued until the metaphyseal region of the bone is prepared to receive and augment, such as tibial augment 60.

As shown in FIG. 2, a prosthetic implant construct is then inserted into the prepared bone, for instance, an assembled tibial baseplate component 70 and tibial augment 60 (as described above) with a stem implant 80. It is understood that other known implant components such as stem extensions and offsets may further contribute to the implant assembly. Further, the implant components described may alternatively be inserted as individual components.

An alternate method of preparing bone, which is not illustrated, would involve preparing a long bone utilizing the system depicted in FIGS. 11 and 12. Guiding element 130 would be inserted into an already prepared central canal region 301, so that fixation features 139 stabilize the guiding element 130. Attachment feature 146 of cutting instrument 140 is then assembled with proximal attachment feature 134 of guiding element 130, so that distal end 141 references the guiding surface 135. The method thereafter closely mirrors that described above in connection with the use of system 10.

Although the invention herein has been described with reference to particular embodiments, it is to be understood that these embodiments are merely illustrative of the principles and applications of the present invention. For example, where the tibial preparation system includes a guiding element having a proximal attachment feature, a femoral preparation system may include a guiding element having a distal attachment feature. It is therefore to be understood that numerous modifications may be made to the illustrative embodiments and that other arrangements may be devised without departing from the spirit and scope of the present invention as defined by the appended claims.

The invention claimed is:

1. A surgical method comprising:
    imaging a bone to create a bone model;
    deriving a guiding surface of a guiding element based upon the bone model;
    associating the guiding element with the bone;
    assembling a cutting instrument with the guiding element by engaging a first attachment feature of the cutting element with a second attachment feature of the guiding element, the second attachment feature adapted to be engaged with the first attachment feature in a manner such that contact between a first region of the cutting instrument and the guiding surface determines the amount of pivot of the cutting instrument about the guiding element;
    preparing the bone by pivoting the cutting instrument about the guiding element; and
    removing the cutting instrument and the guiding element from the prepared bone.

2. The method of claim 1, wherein the imaging step is done pre-operatively.

3. The method of claim 1, further comprising the step of reaming the canal of the bone with a reamer.

4. The method of claim 3, wherein the assembling step includes engaging the guiding element with the reamer.

5. The method of claim 1, further comprising the step of engaging a prosthetic implant with the prepared bone.

6. The method of claim 1, further comprising the step of rotating the cutting instrument about its central axis.

7. The method of claim 1, further comprising the steps of developing a patient specific implant based on the pre-operative imaging of the bone of a patient and engaging the implant with the prepared bone.

8. The method of claim 1, wherein the first attachment feature is an indentation and the second attachment is spherical.

9. The method of claim 8, wherein the first attachment feature is a distal attachment feature and the second attachment feature is a proximal attachment feature.

10. The method of claim 1, wherein the imaging step includes utilizing magnetic resonance imaging, computed tomography or x-ray.

11. A surgical method comprising:
    pre-operatively imaging a bone to create a bone model;
    deriving an implant based upon the bone model;
    deriving a guiding surface of a guiding element based upon the implant;
    reaming a canal of the bone with a reamer;
    inserting the guiding element into the reamed portion of the bone and into engagement with the reamer;
    assembling a cutting instrument with the guiding element by engaging a first attachment feature of the cutting element with a second attachment feature of the guiding element, the second attachment feature adapted to be engaged with the first attachment feature in a manner such that contact between a first region of the cutting instrument and the guiding surface determines the amount of pivot of the cutting instrument about the guiding element;
    preparing the bone by pivoting the cutting instrument about the guiding element;
    removing the cutting instrument and the guiding element from the prepared bone; and engaging the implant with the prepared bone.

* * * * *